(12) United States Patent
Casas

(10) Patent No.: US 11,826,127 B2
(45) Date of Patent: Nov. 28, 2023

(54) INTRA VENTRICULAR AMBULATORY IMPLANTABLE PV LOOP SYSTEM

(71) Applicant: HeartWare, Inc., Miami Lakes, FL (US)

(72) Inventor: Fernando Casas, Miami Lakes, FL (US)

(73) Assignee: HeartWare, Inc., Miami Lakes, FL (US)

( * ) Notice: Subject to any disclaimer, the term of this patent is extended or adjusted under 35 U.S.C. 154(b) by 216 days.

(21) Appl. No.: 17/087,744

(22) Filed: Nov. 3, 2020

(65) Prior Publication Data

US 2021/0045639 A1     Feb. 18, 2021

Related U.S. Application Data

(62) Division of application No. 15/975,936, filed on May 10, 2018, now Pat. No. 10,856,745.

(Continued)

(51) Int. Cl.
*A61B 5/0205* (2006.01)
*A61B 5/0215* (2006.01)
*A61B 5/00* (2006.01)
*A61B 8/06* (2006.01)
*A61B 8/12* (2006.01)
*A61M 60/148* (2021.01)

(Continued)

(52) U.S. Cl.
CPC ........ *A61B 5/0205* (2013.01); *A61B 5/02158* (2013.01); *A61B 5/4836* (2013.01); *A61B 5/686* (2013.01); *A61B 8/06* (2013.01); *A61B 8/12* (2013.01); *A61M 60/148* (2021.01); *A61M 60/178* (2021.01); *A61M 60/216* (2021.01); *A61M 60/419* (2021.01); *A61M 60/422* (2021.01); *A61M 60/515* (2021.01); *A61M 60/538* (2021.01); *A61M 60/857* (2021.01); *A61B 2562/028* (2013.01); *A61M 2205/3344* (2013.01); *A61M 2205/3375* (2013.01); *A61M 2230/30* (2013.01)

(58) Field of Classification Search
CPC ...................................................... A61B 5/0205
USPC .................................................. 600/300–301
See application file for complete search history.

(56) References Cited

U.S. PATENT DOCUMENTS 5,676,644 A   10/1997 Toavs et al.
6,688,861 B2   2/2004 Wampler
(Continued)

FOREIGN PATENT DOCUMENTS

WO        2016004466 A1   1/2016
WO   WO-2017041102 A1 *  3/2017  .......... A61M 1/3678

OTHER PUBLICATIONS

China National Intellectual Property Administration, Notice on the First Office Action and Search Report for corresponding Application No. 201880032538.7, dated Aug. 4, 2021, 19 pages.

(Continued)

*Primary Examiner* — Nicole F Lavert
(74) *Attorney, Agent, or Firm* — Shumaker & Sieffert, P.A.

(57) ABSTRACT

A blood pump including a housing having an inlet element, the inlet element including a distal portion coupled to the housing and a proximal portion sized to be received within at least a portion of a heart of a patient and a rotor configured to rotate within the housing and impel blood from the heart. At least one pressure sensor is coupled to the proximal portion of the inlet element.

19 Claims, 5 Drawing Sheets

Related U.S. Application Data

(60) Provisional application No. 62/506,833, filed on May 16, 2017.

(51) Int. Cl.
  *A61M 60/419* (2021.01)
  *A61M 60/857* (2021.01)
  *A61M 60/422* (2021.01)
  *A61M 60/538* (2021.01)
  *A61M 60/515* (2021.01)
  *A61M 60/216* (2021.01)
  *A61M 60/178* (2021.01)

(56) References Cited

U.S. PATENT DOCUMENTS

| | | | |
|---|---|---|---|
| 7,575,423 | B2 | 8/2009 | Wampler |
| 7,976,271 | B2 | 7/2011 | LaRose et al. |
| 3,007,254 | A1 | 8/2011 | LaRose et al. |
| 8,419,609 | B2 | 4/2013 | Shambaugh, Jr. et al. |
| 8,512,013 | B2 | 8/2013 | LaRose et al. |
| 8,562,507 | B2* | 10/2013 | Poirier ................ A61M 60/148 600/16 |
| 10,856,745 | B2 | 12/2020 | Casas |
| 2003/0032853 | A1* | 2/2003 | Korakianitis ....... A61M 60/569 600/16 |
| 2006/0222533 | A1* | 10/2006 | Reeves ............... A61M 1/3659 417/423.1 |
| 2006/0235357 | A1 | 10/2006 | Woodward et al. |
| 2010/0268334 | A1 | 10/2010 | Pate et al. |
| 2012/0065528 | A1* | 3/2012 | Gill ...................... A61B 5/7239 600/509 |
| 2014/0005706 | A1* | 1/2014 | Gelfand ................ A61N 7/022 606/169 |
| 2014/0350401 | A1* | 11/2014 | Sinelnikov ......... A61B 18/1492 606/169 |
| 2014/0371849 | A1 | 12/2014 | Orejola et al. |
| 2015/0051438 | A1 | 2/2015 | Taskin |
| 2015/0290372 | A1 | 10/2015 | Muller et al. |
| 2015/0314058 | A1* | 11/2015 | O'Mahony ............ G01B 7/003 417/63 |
| 2017/0049949 | A1* | 2/2017 | Gilmanshin ......... B01D 21/286 |
| 2017/0112988 | A1 | 4/2017 | Rosenberg et al. |
| 2017/0128646 | A1 | 5/2017 | Karch |
| 2017/0281840 | A1 | 10/2017 | LaRose et al. |

OTHER PUBLICATIONS

International Preliminary Report on Patentability from International Application No. PCT/US2018/031971, dated Nov. 19, 2019, 10 pp.
Notice of Intent to Grant and Text Intended to Grant from counterpart European Application No. 18727593.8 dated Nov. 16, 2021, 39 pp.
Prosecution History from U.S. Appl. No. 15/975,936 filed from Feb. 10, 2020 through Oct. 5, 2020, 48 pp.
Response to Communication Pursuant to Rules 161(1) and 162 EPC dated Jan. 3, 2020, from counterpart European Application No. 18727593.8, filed Jun. 3, 2020, 8 pp.
Annex to Form PCT/ISA/206, Communication Relating to the Search Results of the Partial International Search, for corresponding International Application No. PCT/US2018/031971; International Filing Date: May 10, 2018 consisting of 10-pages.
International Search Report and Written Opinion, for corresponding International Application No. PCT/US2018/031971; International Filing Date: May 10, 2018 consisting of 18-pages.
Decision on Rejection, and translation thereof, from counterpart Chinese Application No. 201880032538.7 dated Jun. 6, 2022, 8 pp.

\* cited by examiner

INTRA VENTRICULAR AMBULATORY IMPLANTABLE PV LOOP SYSTEM

CROSS-REFERENCE TO RELATED APPLICATION

This application is a divisional of U.S. patent application Ser. No. 15/975,936, filed May 10, 2018, which granted as U.S. Pat. No. 10,856,745, on Dec. 8, 2020, which is related to and claims priority to U.S. Provisional Patent Application Ser. No. 62/506,833, filed May 16, 2017, entitled "INTRA VENTRICULAR AMBULATORY IMPLANTABLE PV LOOP SYSTEM," the entirety of each of which is incorporated herein by reference.

STATEMENT REGARDING FEDERALLY SPONSORED RESEARCH OR DEVELOPMENT n/a

TECHNICAL FIELD

This disclosure relates to a method and system for a blood pump having sensors configured to measure the efficiency of the heart.

BACKGROUND

Implantable blood pumps used as mechanical circulatory support devices or "MCSDs" include a pumping mechanism to move blood from the heart out to the rest of the body. The pumping mechanism may be a centrifugal flow pump, such as the HVAD® Pump manufactured by HeartWare, Inc. in Miami Lakes, Fla., USA. The HVAD® Pump is further discussed in U.S. Pat. No. 8,512,013, the disclosure of which is hereby incorporated herein in its entirety. In operation, the blood pump draws blood from a source such as the right ventricle, left ventricle, right atrium, or left atrium of a patient's heart and impels the blood into an artery such as the patient's ascending aorta or peripheral artery.

However, after such devices are implanted, it is difficult to determine whether the diseased part of the heart is healing and functioning within normal parameters. That is, because the blood pump is assisting with pumping blood either from one part of the heart to another or from the heart to the lungs or the rest of the body, it is difficult to determine if, for example, the left or right ventricle is functioning normally or if it remains malfunctioning. For example, patients may undergo catheterization in a hospital setting to determine heart functionality, i.e. a PV loop analysis, however, such procedures are invasive and only provide a brief snapshot of the health of the heart.

SUMMARY

Some embodiments advantageously provide a method and system for a blood pump, including a housing including an inlet element, the inlet element having a distal portion coupled to the housing and a proximal portion sized to be received within at least a portion of a heart of a patient and a rotor configured to rotate within the housing and impel blood from the heart. At least one pressure sensor is coupled to the proximal portion of inlet element.

In another aspect of this embodiment, the device includes a flange member at least partially disposed around the proximal portion of the inlet element, and wherein the pressure sensor is coupled to the flange member.

In another aspect of this embodiment, the inlet element defines a first diameter, and wherein the flange member defines a second diameter larger than the first dimeter.

In another aspect of this embodiment, the device includes an ultrasonic transducer coupled to the distal portion of the inlet element.

In another aspect of this embodiment, the ultrasonic transducer is coupled to the flange member.

In another aspect of this embodiment, the ultrasonic transducer and the pressure sensor are coupled to a microelectromechanical system ("MEMS").

In another aspect of this embodiment, the MEMS is configured to be adhered to the flange member.

In another aspect of this embodiment, the housing further includes a stator having a plurality of coils, and wherein the stator is configured to generate a magnetic force to rotate the rotor, and wherein the stator includes a plurality of conductors configured to couple with a power source.

In another aspect of this embodiment, the plurality of conductors are electrically coupled to the MEMS.

In another aspect of this embodiment, the MEMS includes a wireless transmitter, and wherein the ultrasonic transducer and the pressure sensor are in communication with a wireless transmitter coupled to the inlet element.

In another aspect of this embodiment, the device further includes a flange member at least partially disposed around the proximal portion of the inlet element, and wherein an ultrasonic sensor is coupled to the flange member.

In another embodiment, a method of measuring an efficiency of a patient's heart includes inserting an inlet element of a blood pump within a chamber of the patient's heart, the inlet element including at least one pressure sensor and at least one ultrasonic transducer. The pressure of the chamber is measured with the at least one pressure sensor. The volume of the chamber is measured with the at least one ultrasonic transducer.

In another aspect of this embodiment, the method further includes determining an efficiency of the chamber of the patient's heart based on the measurements of the pressure and volume within the chamber.

In another aspect of this embodiment, the blood pump further includes a flange member at least partially disposed around the inlet element, and wherein the at least one pressure sensor is coupled to the flange member.

In another aspect of this embodiment, the flange member includes a proximal and a distal end, and wherein the proximal end of the flange member is inserted within the chamber of the heart, and wherein the at least one pressure sensor is coupled to the proximal end of the flange member.

In another aspect of this embodiment, the at least one ultrasonic transducer is coupled to the proximal end of the flange member.

In another aspect of this embodiment, the blood pump includes a housing, and wherein the housing includes a stator having a plurality of coils, and wherein the stator is configured to generate a magnetic force to rotate the rotor, and wherein the stator includes a plurality of conductors configured to couple with a power source.

In another aspect of this embodiment, the at least one ultrasonic transducer and the at least one pressure sensor are coupled to a MEMS.

In another aspect of this embodiment, the MEMS is configured to be adhered to the flange member.

In another embodiment, a blood pump system is provided including a housing having an inlet element, the inlet element having a distal portion coupled to the housing and a proximal portion sized to be received within at least a portion of a heart of a patient. A rotor is configured to rotate within the housing and impel blood from the heart. Two stators are included, each stator has a plurality of coils, and each stator is configured to generate a magnetic force to rotate the rotor and includes a plurality of conductors configured to couple with a power source. A flange member is disposed around a circumference of the proximal portion of the inlet element, the flange member includes a MEMS coupled to the plurality of conductors and adheres to a proximal surface of the flange member. A pressure sensor and an ultrasonic transducer are coupled to the MEMS.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

As used herein, relational terms, such as "first" and "second," "top" and "bottom," and the like, may be used solely to distinguish one entity or element from another entity or element without necessarily requiring or implying any physical or logical relationship or order between such entities or elements.

Figure 1:
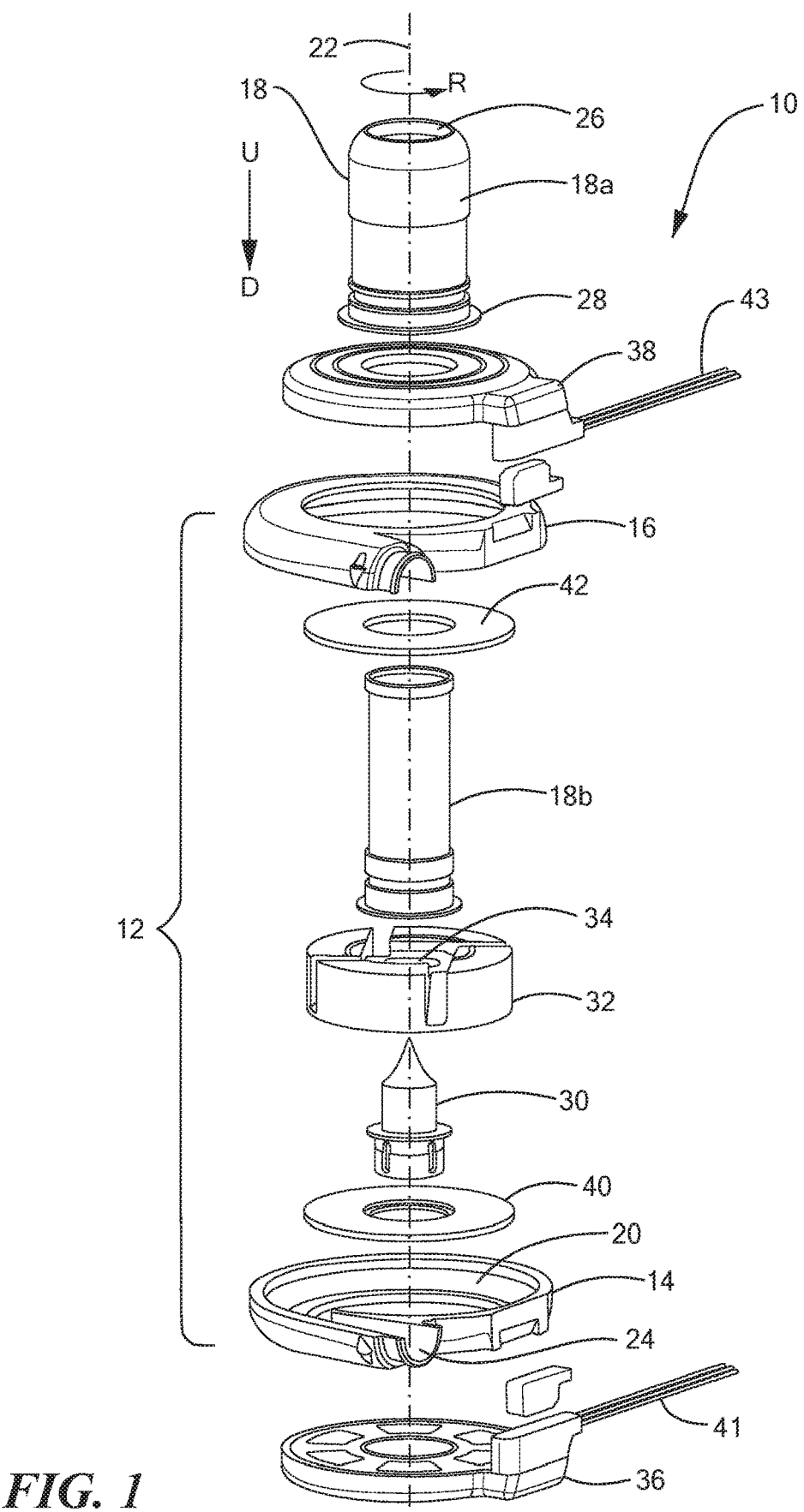
FIG. 1 is an exploded view of exemplary blood pump constructed in accordance with the principles of the present application.

Referring now to the drawings in which like reference designators refer to like elements there is shown in FIG. 1 an exemplary blood pump constructed in accordance with the principles of the present application and designated generally "10." The blood pump 10, according to one embodiment of the disclosure, includes a static structure or housing 12 which houses the components of the blood pump 10. In one configuration, the housing 12 includes a lower housing or first portion 14, an upper housing or second portion 16, and an inlet element 18 or inflow cannula 18 which includes an outer tube 18a and an inner tube 18b. The first portion 14 and the second portion 16 cooperatively define a volute shaped chamber 20 having a major longitudinal axis 22 extending through the first portion 14 and the inflow cannula 18. The chamber 20 defines a radius that increases progressively around the axis 22 to an outlet location on the periphery of the chamber 20. The first portion 14 and the second portion 16 define an outlet 24 in communication with chamber 20. The first portion 14 and the second portion 16 also define isolated chambers (not shown) separated from the volute chamber 20 by magnetically permeable walls. The inflow cannula 18 is generally cylindrical and extends generally from the first portion 14 along the axis 22. The inflow cannula 18 has an upstream end or proximal end 26 remote from second portion 16 and a downstream end or distal end 28 proximate the chamber 20.

The parts of the housing 12 mentioned above are fixedly connected to one another so that the housing 12 as a whole defines a continuous enclosed flow path. The flow path extends from the upstream end 26 at the upstream end of the flow path to the outlet 24 at the downstream end of the flow path. The upstream and downstream directions along the flow path are indicated in by the arrows U and D, respectively. A post 30 is mounted to the first portion 14 along the axis 22. A generally disc shaped ferromagnetic rotor 32 with a central hole 34 is mounted within the chamber 20 for rotation about the axis 22. The rotor 32 includes a permanent magnet and flow channels for transferring blood from adjacent the center of the rotor 32 to the periphery of the rotor 32. In the assembled condition, the post 30 is received in the central hole of the rotor 32.

A first stator 36 having a plurality of coils may be disposed within the first portion 14 downstream from the rotor 32. The first stator 36 may be axially aligned with the rotor along the axis 22 such that when a current is applied to the coils in the first stator 36, the electromagnetic forces generated by the first stator 36 rotate the rotor 32 and pump blood. A second stator 38 may be disposed within the second portion 16 upstream from the rotor 32. The second stator 38 may be configured to operate in conjunction with or independently of the first stator 36 to rotate the rotor 32.

Electrical connectors 41 and 43 (FIG. 1) are provided on the first portion 14 and the second portion 16, respectively, for connecting the coils to a source of power, such as a controller (not shown). The controller is arranged to apply power to the coils of the pump to create a rotating magnetic field which spins the rotor 32 around the axis 22 in a predetermined first direction of rotation, such as the direction R indicated by the arrow which is counterclockwise as seen from the upstream end of the inflow cannula 18. In other configurations of the blood pump 10, the first direction may be clockwise. Rotation of the rotor 32 impels blood downstream along the flow path so that the blood, moves in a downstream direction D along the flow path, and exits through the outlet 24. During rotation, hydrodynamic and magnetic bearings (not shown) support the rotor 32 and maintain the rotor 32 out of contact with the surfaces of the elements of the first portion 14 and the second portion 16 during operation.

A first non-ferromagnetic disk 40 may be disposed within the first portion 14 upstream from the rotor 32 between the first stator 36 and the rotor 32 and a second non-ferromagnetic disk 42 may be disposed downstream from the rotor 32 within the second portion 16 between the second stator 38 and the rotor 32. The rotor 32 is configured to rotate between the first disk 40 and the second disk 42 without contacting either disk. The general arrangement of the components described above may be similar to the blood pump 10 used in the MCSD sold under the designation HVAD® by Heart-Ware, Inc., assignee of the present application. The arrangement of components such as the magnets, electromagnetic coils, and hydrodynamic bearings used in such a pump and variants of the same general design are described in U.S. Pat. Nos. 6,688,861; 7,575,423; 7,976,271; and 8,419,609, the disclosures of which are hereby incorporated by reference herein.

Figure 2:
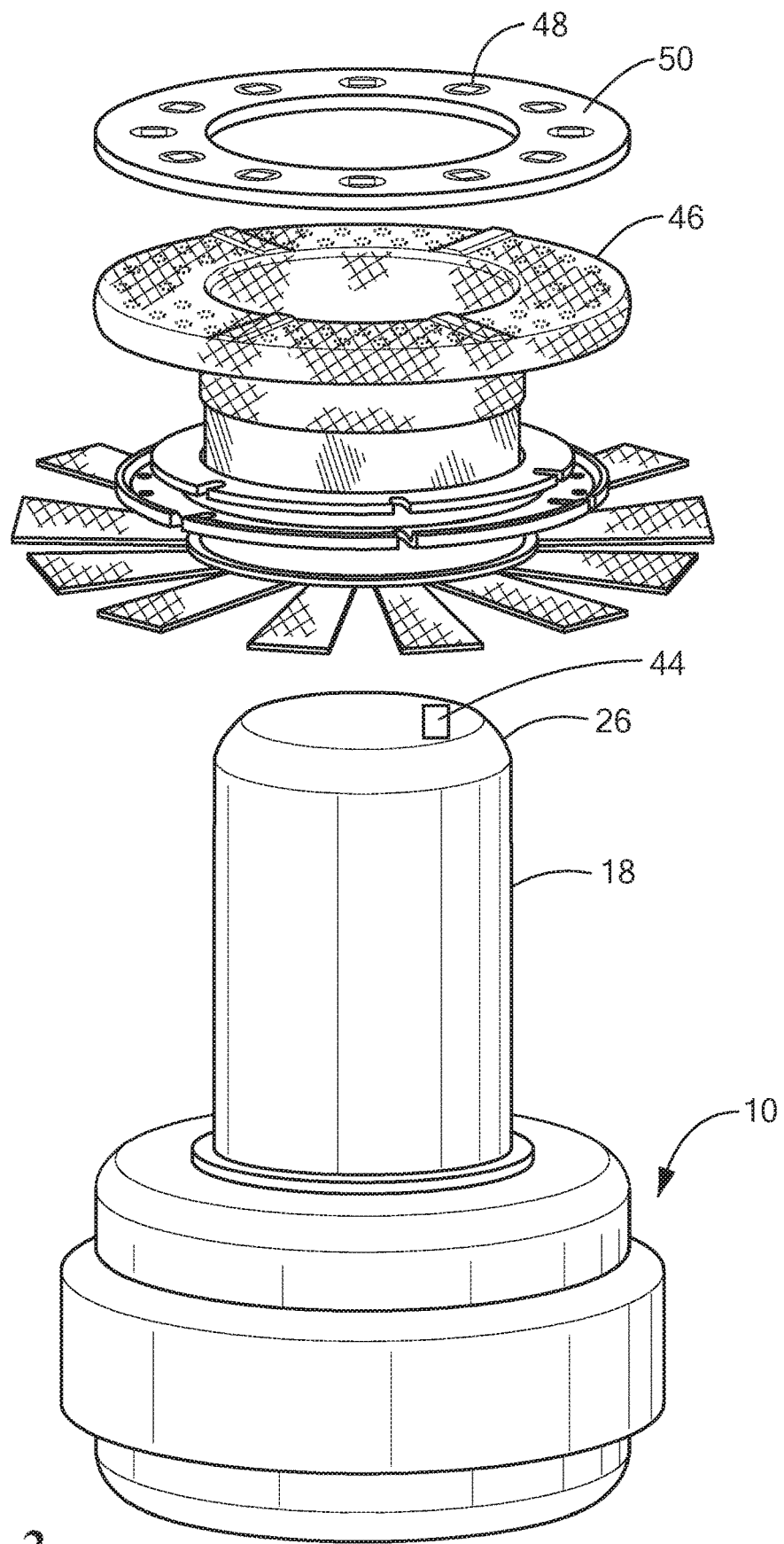
FIG. 2 is front view of a portion of the assembled blood pump shown in FIG. 1 with a mounting element, flange member, and MEMS device.
Figure 3:
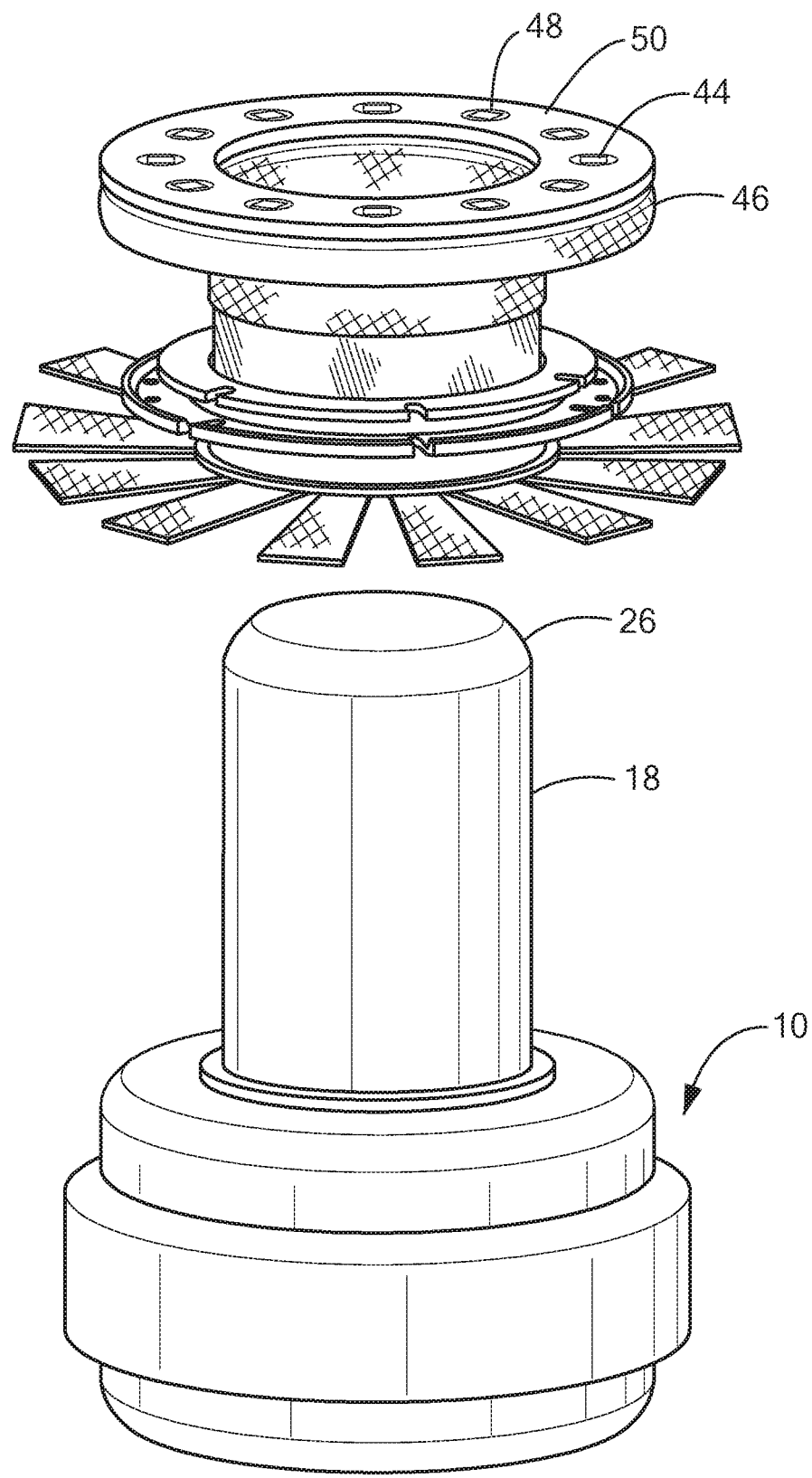
FIG. 3 is a front view of the assembly shown in FIG. 1 with the MEMS device mounting to the MEMS device.

Referring now to FIGS. 2-3, coupled to the proximal end 26 of the inlet element 18 may be a pressure sensor 44 configured to measure the blood pressure within any one chamber of the heart. For example, the proximal end 26 may include one or an array of pressure transducers configured to measure the changing pressure within a particular chamber of the heart as the heart contracts and relaxes. In one configuration, the pressure sensor 44 is coupled to the most proximal end of the inlet element 18 without blocking the opening in the inlet element 18 and is received within the left ventricle, although the inlet element 18 may be at least partially insertable within any chamber of the heart.

The pressure sensor 44 may be coupled to a flange member 46 (FIGS. 2 and 3), as described in U.S. patent application Ser. No. 15/471,575, the entirety of which is incorporated by reference. The flange member 46 functions to prevent thrombus from entering the inlet element 18. In addition, the flange member 46 is configured to be coupled to the proximal end of the inlet element 18 and defines a diameter larger than that of the inlet element 18. The most proximal end of the flange member 46 is the surface of the flange member 46 that is facing the interior of the particular chamber in which it is inserted.

An ultrasound transducer 48 may further be coupled to the proximal end 26 of the inlet element 18 or the flange member 46. The ultrasound transducer 48 may include one or an array of ultrasound transducers configured to measure the volume within a chamber of the heart as the heart contracts and relaxes. In one configuration, a microelectromechanical system (MEMS) device 50 may be adhered to or otherwise coupled to the surface of the flange member 46 and the pressure sensor 44 and the ultrasonic transducer 48 may be integrated as arrays into the surface of the MEMS device 50. For example, the MEMS device 50 may be a sticker that is adhered to the flange member 46 or alternatively may be attached or etched into the surface of the flange member 46. The MEMS device 50 may be coupled to an independent voltage source (not shown) or the voltage source configured to power the pump 10. The MEMS device 50 may further include a wireless transmitter and receiver (not shown) such that information measured by the ultrasonic transducer 48 and/or the pressure sensor 44 may be transmitted to a remote controller (not shown) outside of the patient.

In an exemplary configuration, the most proximal end 26 of the inlet element 18 is inserted within the left ventricle of the patient. The flange member 46 may be positioned on the proximal end 26, as described U.S. patent application Ser. No. 15/471,575 referenced above. The MEMS device 50 may be adhered to the flange member 46 prior to affixation to the inlet element 18.

The pressure sensor 44 and the ultrasonic transducer 48 be in the form of independently activated sensors in an array such that multiple measurements along multiple vectors may be measured. For example, the pressure sensors 44 may be included on the MEMS device 50 or directly on the flange member 46. As the measured pressure may be variable during the diastole and systole cycle and may be variable based on the position of the sensor 44 with respect to the chamber, the MEMS device 50 may be configured to individually activate the pressure sensors 44 of the array on the MEMS device to make multiple measurements either simultaneously or sequentially.

Figure 4:
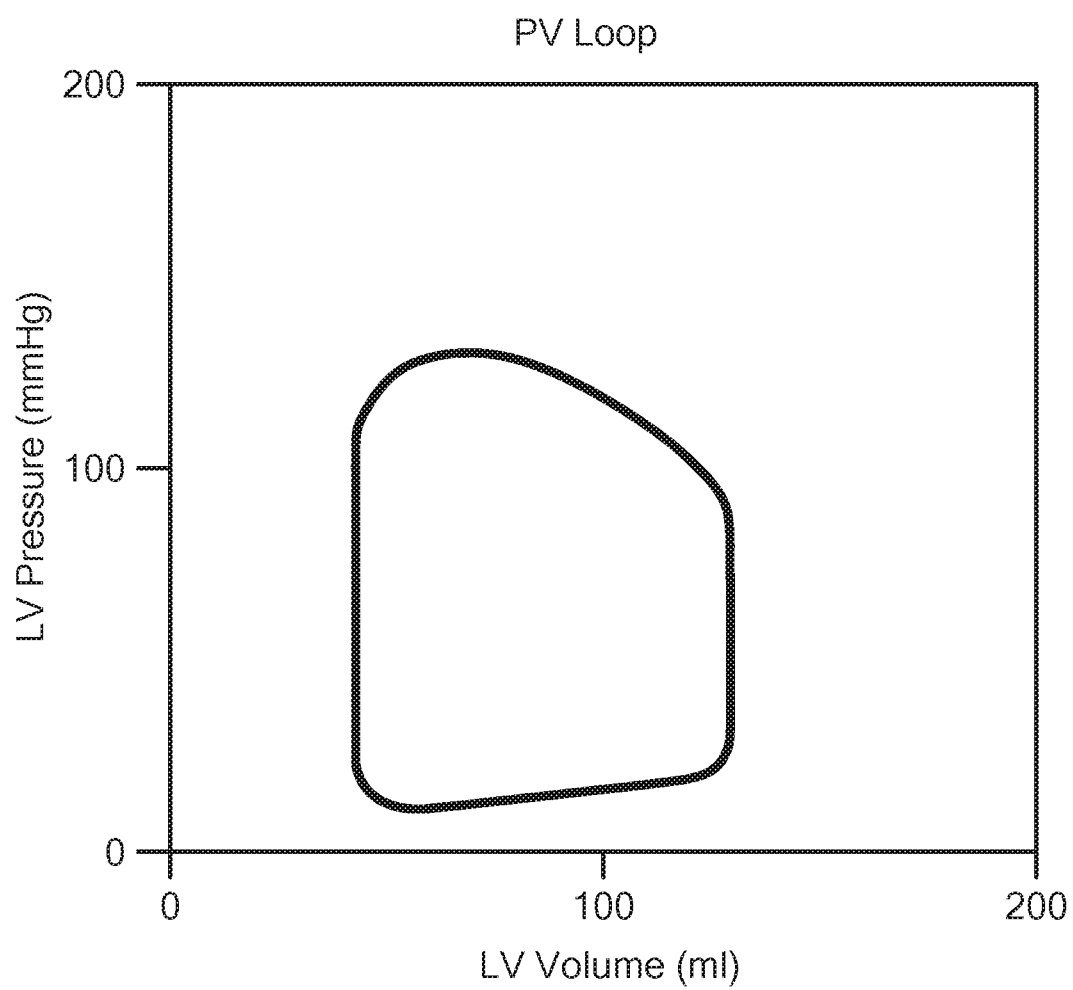
FIG. 4 is a Pressure-Volume (PV) loop of a cardiac cycle.

Similar to the pressure sensor 44, the ultrasonic transducer 48 may be in the form of an array of ultrasonic transducers 48 facing different directions on the MEMS device 50 to create different vectors of measurement within the left ventricle, for example. Owing to the position of the ultrasonic transducer 48 on the MEMS device 50 when implanted within the left ventricle and owing to the shape of the left ventricle, to measure the volume of the left ventricle, the array of ultrasonic transducers 48 may be configured to sweep across the left ventricle. In particular, such sweeping may include ultrasonic transducers 48 either having a scanning range or being movable to angle themselves to measure the volume of the left ventricle. In one configuration, a first plurality of the ultrasonic transducers 48 may be timed to measure the volume of the left ventricle during systole and another plurality of the ultrasonic transducers 48 may be timed to measure the volume of the left ventricle during diastole. The combined pressure and volume measurements may be used to produce a PV loop, as shown in FIG. 4, to measure the efficiency of the particular chamber of the heart in real time.

Figure 5:
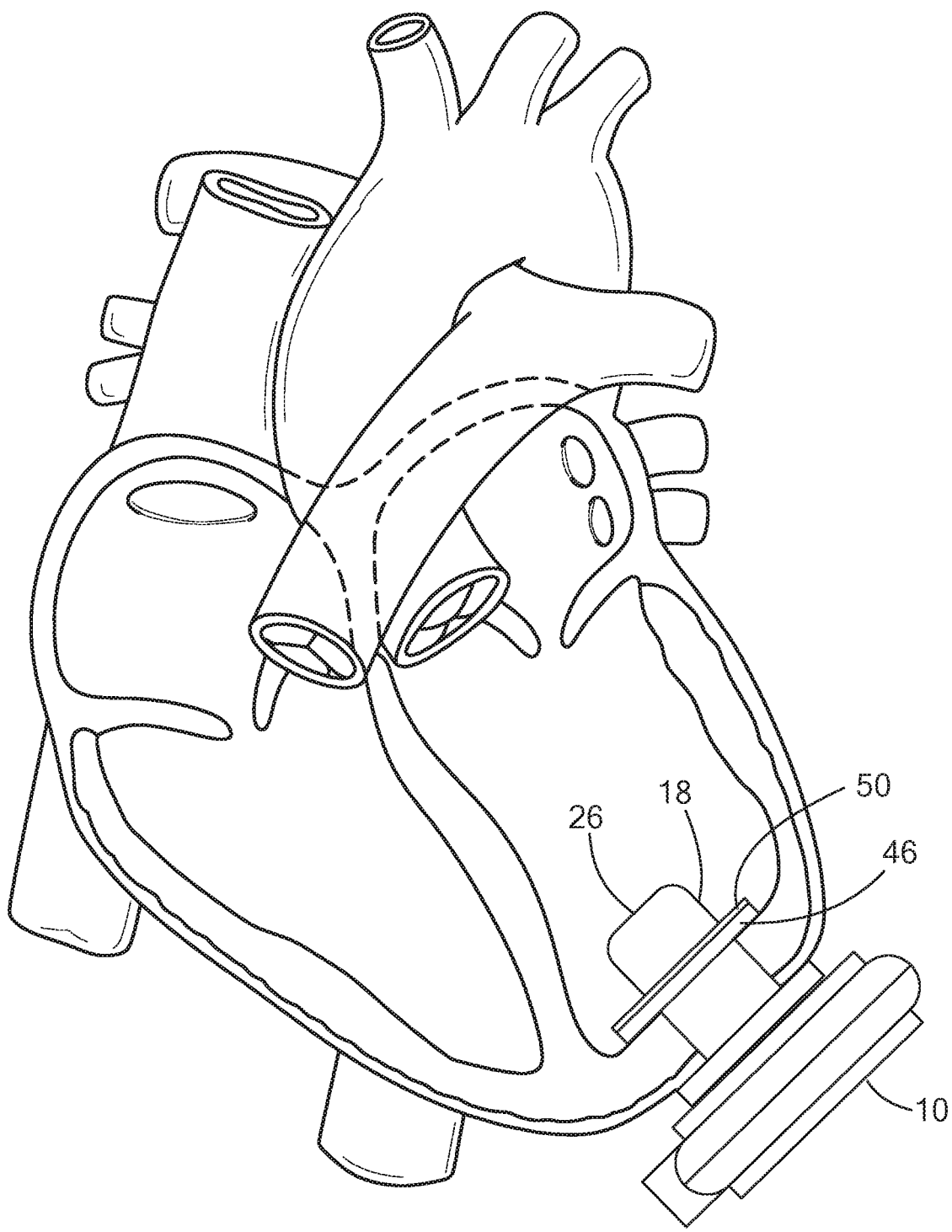
FIG. 5 shows the device of FIG. 2 implanted within the left ventricle of the heart.

With reference to FIG. 5, as discussed above, in one exemplary configuration, the proximal end 26 of the inlet element 18 of the blood pump 10 is inserted within the left ventricle of the heart. The flange member 46 is coupled to the inlet element 18 with the MEMS device 50 being coupled to the surface of the flange member 46 which faces the interior of the left ventricle such that the measurements of the pressure and/or volume within the left ventricle may be obtained.

Although the above embodiments are described with respect to a dual stator system, it is contemplated that the above sensors may be used in the manner describe herein in axial flow pumps having a single stator, as described in U.S. Pat. No. 8,007,254 and U.S. Patent Application Publication No. 2015/0051438 A1, sold under the designation MVAD® by HeartWare, Inc., assignee of the present application. Moreover, the embodiments described above are independent from the type of pump. For example, the sensor array described above may be positioned on any supporting device configured to hold the pump either to the heart or within the heart. In one configuration, the sensor array may continue to work after the pump is removed and replaced by a plug, for example, as the grommet/sewing ring implanted in the apex of the heart would remain in place.

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings without departing from the scope of the following claims.

What is claimed is:

1. A method of measuring an efficiency of a patient's heart, comprising:
   inserting an inlet element of a blood pump within a chamber of the patient's heart, the inlet element including at least one pressure sensor and at least one ultrasonic transducer;
   measuring a pressure of the chamber with the at least one pressure sensor; and
   measuring a volume of the chamber with the at least one ultrasonic transducer.

2. The method of claim 1, further comprising determining an efficiency of the chamber of the patient's heart based on the measured pressure and the measured volume within the chamber.

3. The method of claim 1, wherein the blood pump further includes a flange member at least partially disposed around the inlet element, and wherein the at least one pressure sensor is coupled to the flange member.

4. The method of claim 3, wherein the flange member includes a proximal and a distal end, and wherein the proximal end of the flange member is inserted within the chamber of the heart, and wherein the at least one pressure sensor is coupled to the proximal end of the flange member.

5. The method of claim 4, wherein the at least one ultrasonic transducer is coupled to the proximal end of the flange member.

6. The method of claim 5, wherein the at least one ultrasonic transducer and the at least one pressure sensor are coupled to a MEMS.

7. The method of claim 6, wherein the MEMS is configured to be adhered to the flange member.

8. The method of claim 1, wherein the blood pump includes a housing, and wherein the housing includes a stator having a plurality of coils, and wherein the stator is configured to generate a magnetic force to rotate a rotor, and wherein the stator includes a plurality of conductors configured to couple with a power source.

9. The method of claim 1, wherein the at least one ultrasonic sensor includes an array of independently activatable ultrasonic sensors facing different directions.

10. The method of claim 1, wherein the at least one pressure sensor includes an array of independently activatable pressure sensors.

11. The method of claim 1, wherein the chamber is a left ventricle of the heart.

12. A method comprising:
   measuring, by at least one pressure sensor, a pressure in a chamber of a heart of a patient, wherein an inlet element of a blood pump includes the at least one pressure sensor; and
   measuring, by at least one ultrasonic transducer, a volume of the chamber, wherein the inlet element includes the at least one ultrasonic transducer; and
   determining an efficiency of the chamber of the heart based on the measured pressure and the measured volume within the chamber.

13. The method of claim 12, wherein the at least one ultrasonic transducer includes an array of ultrasonic transducers facing different directions, and wherein measuring the volume of the chamber comprises measuring the volume along multiple sensing vectors.

14. The method of claim 12, wherein the at least one ultrasonic transducer includes an array of ultrasonic transducers facing different directions, and wherein measuring the volume of the chamber comprises:
   measuring, using a first plurality of ultrasonic transducers of the array of ultrasonic transducers, the volume of the chamber at a first time; and
   measuring, using a second plurality of ultrasonic transducers of the array of ultrasonic transducers, the volume of the chamber at a second time.

15. The method of claim 14, wherein the first time is during systole and the second time is during diastole.

16. The method of claim 12, wherein the at least one pressure sensor includes an array of pressure sensors facing different directions, and wherein measuring the pressure in the chamber comprises measuring the pressure along multiple sensing vectors.

17. The method of claim 12, wherein the at least one pressure sensor includes an array of pressure sensors facing different directions, and wherein measuring the pressure comprises:
   measuring, using a first plurality of pressure sensors of the array of pressure sensors, the pressure in the chamber at a first time; and
   measuring, using a second plurality of pressure sensors of the array of pressure sensors, the pressure in the chamber at a second time.

18. The method of claim 17, wherein the first time is during systole and the second time is during diastole.

19. The method of claim 12, wherein the chamber is a left ventricle of the heart.

* * * * *